(12) United States Patent
Palmer et al.

(10) Patent No.: US 8,657,840 B2
(45) Date of Patent: *Feb. 25, 2014

(54) SURGICAL INSTRUMENT WITH DISTAL SUCTION CAPABILITY

(71) Applicant: Gyrus ENT L.L.C., Bartlett, TN (US)

(72) Inventors: Allen Palmer, Arlington, TN (US); John Flynn, Collierville, TN (US); Sean Corrigan, Chicago, IL (US); Tom Matusaitis, Chicago, IL (US); Ed Geiselhart, Chicago, IL (US); Carolyn Rose, Chicago, IL (US); Antonio Belton, Richton Park, IL (US)

(73) Assignee: Gyrus Ent L.L.C., Bartlett, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,355

(22) Filed: May 31, 2013

(65) Prior Publication Data
US 2013/0261600 A1 Oct. 3, 2013

Related U.S. Application Data

(63) Continuation of application No. 13/029,588, filed on Feb. 17, 2011, now Pat. No. 8,475,482.

(51) Int. Cl.
*A61B 17/32* (2006.01)
(52) U.S. Cl.
USPC .......................................... 606/170
(58) Field of Classification Search
USPC ............ 600/562, 564–566; 604/22; 606/167, 606/168, 170–172, 180
See application file for complete search history.

(56) References Cited

U.S. PATENT DOCUMENTS

| | | |
|---|---|---|
| 3,834,388 A | 9/1974 | Sauer |
| 3,882,872 A | 5/1975 | Douvas et al. |
| 3,929,126 A | 12/1975 | Corsaut |
| 3,937,222 A | 2/1976 | Banko |
| 4,002,170 A | 1/1977 | Hansen et al. |
| 4,014,333 A | 3/1977 | McIntyre |
| 4,058,121 A | 11/1977 | Choksi et al. |
| 4,114,625 A | 9/1978 | Onat |
| 4,180,068 A | 12/1979 | Jacobsen et al. |
| 4,311,140 A | 1/1982 | Bridgman |
| 4,451,257 A | 5/1984 | Atchley |

(Continued)

OTHER PUBLICATIONS

Nov. 23, 2012 Office Action issued in U.S. Appl. No. 13/029,588.

(Continued)

*Primary Examiner* — Ashley Fishback
(74) *Attorney, Agent, or Firm* — Oliff, PLC

(57) ABSTRACT

A surgical instrument including a main unit and a suction conduit. The main unit includes at least one tubular body having a distal end, a proximal end, and an inlet disposed near the distal end. The suction conduit is slidably disposed over the main unit, and is slidably movable along the main unit between a retracted position, at which the suction conduit does not cover the inlet of the main unit, and an extended position at which the suction conduit covers the inlet of the main unit and a suction inlet of the suction conduit is placed in fluid-communication with the main unit inlet. The surgical instrument can be used as a suction tool by placing the suction conduit in the extended position and applying a vacuum through the inlet of the main unit and the suction inlet.

18 Claims, 7 Drawing Sheets

(56) References Cited

U.S. PATENT DOCUMENTS

| | | |
|---|---|---|
| 4,487,600 A | 12/1984 | Brownlie et al. |
| 4,535,773 A | 8/1985 | Yoon |
| 4,573,979 A | 3/1986 | Blake |
| 4,594,074 A | 6/1986 | Andersen et al. |
| 4,648,871 A | 3/1987 | Jacob |
| 4,690,672 A | 9/1987 | Veltrup |
| 4,844,064 A | 7/1989 | Thimsen et al. |
| 4,869,717 A | 9/1989 | Adair |
| 4,886,491 A | 12/1989 | Parisi et al. |
| 5,084,013 A | 1/1992 | Takase |
| 5,163,912 A | 11/1992 | Gay et al. |
| 5,236,414 A | 8/1993 | Takasu |
| 5,248,297 A | 9/1993 | Takase |
| 5,254,128 A | 10/1993 | Mesa |
| 5,354,291 A | 10/1994 | Bales et al. |
| 5,423,764 A | 6/1995 | Fry |
| 5,505,710 A | 4/1996 | Dorsey, III |
| 5,601,585 A * | 2/1997 | Banik et al. ............ 606/180 |
| 5,674,235 A | 10/1997 | Parisi |
| 5,709,698 A | 1/1998 | Adams et al. |
| 5,730,752 A | 3/1998 | Alden et al. |
| 5,766,194 A | 6/1998 | Smith |
| 5,779,662 A | 7/1998 | Berman |
| 6,342,061 B1 | 1/2002 | Kauker et al. |
| 6,428,498 B2 | 8/2002 | Uflacker |
| 6,540,713 B1 | 4/2003 | Cimino |
| 6,752,768 B2 | 6/2004 | Burdorff et al. |
| 6,752,782 B2 * | 6/2004 | Liao ............................ 604/110 |
| 6,875,173 B2 | 4/2005 | Suddaby |
| 6,902,558 B2 | 6/2005 | Laks |
| 7,066,914 B2 | 6/2006 | Andersen |
| 7,247,161 B2 | 7/2007 | Johnston et al. |
| 7,318,831 B2 | 1/2008 | Alvarez et al. |
| 7,537,594 B2 | 5/2009 | Sartor |
| 8,012,141 B2 | 9/2011 | Wright et al. |
| 8,092,415 B2 | 1/2012 | Moehle et al. |
| 8,292,841 B2 | 10/2012 | Gregersen |
| 8,475,482 B2 | 7/2013 | Palmer et al. |
| 2003/0163126 A1 | 8/2003 | West, Jr. |
| 2003/0181904 A1 | 9/2003 | Levine et al. |
| 2007/0016099 A1 * | 1/2007 | Chin et al. .................. 600/565 |
| 2011/0196400 A1 | 8/2011 | Robertson et al. |
| 2012/0191116 A1 | 7/2012 | Flynn et al. |
| 2012/0191117 A1 | 7/2012 | Palmer et al. |

OTHER PUBLICATIONS

Apr. 8, 2013 Notice of Allowance issued in U.S. Appl. No. 13/029,588.

* cited by examiner

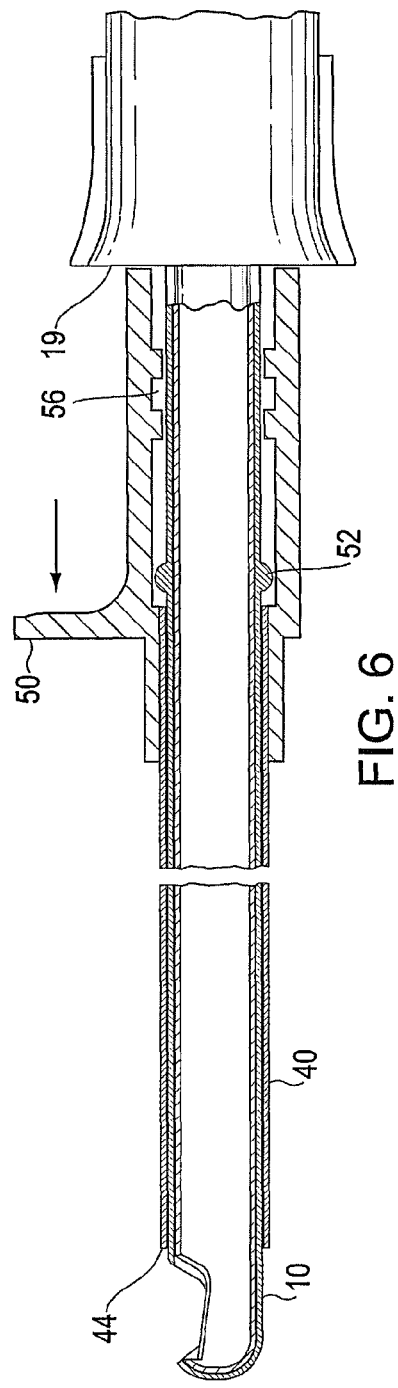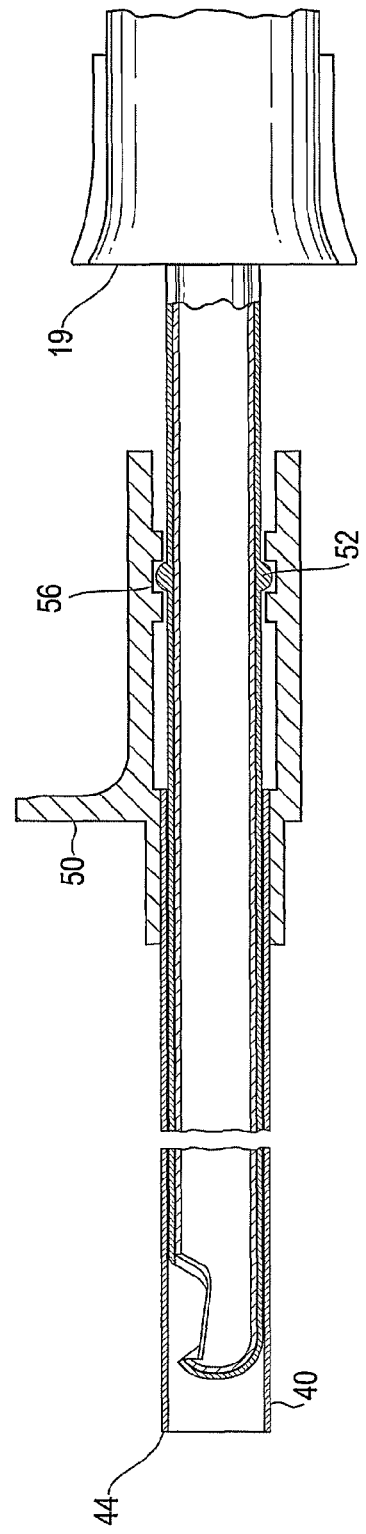

SURGICAL INSTRUMENT WITH DISTAL SUCTION CAPABILITY

This is a continuation of U.S. patent application Ser. No. 13/029,588 filed Feb. 17, 2011 (now U.S. Pat. No. 8,475,482), the disclosure of which is incorporated herein by reference in its entirety.

BACKGROUND

This disclosure relates to surgical instruments that use suction.

Many surgical instruments use suction, for example, to remove material such as tissue and fluids from the operating site. Such instruments often include the suction capability in addition to other functions performed by the instrument. For example, many surgical instruments that are used to shave, cut, resect, abrade and/or remove tissue, bone and/or other bodily materials are known and include a suction capability. Such surgical instruments can include a cutting surface, such as a rotating blade disposed on an elongated inner tube that is rotated within an elongated outer tube having a cutting window. The inner and outer tubes together form a surgical cutting instrument or unit. In general, the elongated outer tube includes a distal end defining an opening or cutting window disposed at a side of the distal end of the outer tube. The cutting window of the outer tube exposes the cutting surface of the inner tube (located at a distal end of the inner tube) to tissue, bone and/or any other bodily materials to be removed. A powered handpiece is used to rotate the inner tube with respect to the outer tube while an outer tube hub (connected to the proximal end of the outer tube) is fixed to the handpiece and an inner tube hub (connected to the proximal end of the inner tube) is loosely held in place by the powered handpiece.

In some instruments the inner tube is hollow and has a cutting window on a side surface of its distal end such that tissue, bone, etc. will be cut or shaved as the cutting window of the inner tube aligns with and then becomes misaligned with the cutting window of the outer tube as the inner tube is rotated within the outer tube. In this regard, it can be said that the cutting device nibbles or takes away small pieces of the bone, tissue, etc. as the inner tube is rotated within the outer tube.

In some instruments a vacuum is applied through the inner tube such that the bodily material that is to be cut, shaved, etc. is drawn into the windows of the inner and outer tubes when those windows become aligned, thereby facilitating the cutting, shaving, etc. of the tissue, which then travels through the inner tube due to the suction. It also is common to supply an irrigation fluid, which can include a liquid, to the surgical site via a passage provided between the inner and outer tubes.

SUMMARY

Many times during surgery, the surgeon wishes to apply suction to the surgical site without performing cutting or any other operation(s) that is/are performed with the surgical instrument. This usually is done by withdrawing the surgical instrument and inserting a dedicated suction device (for example, a suction wand which is a tube to which suction is applied). However, exchanging the surgical instrument for the dedicated suction device is time-consuming. Furthermore, insertion and removal of instruments into the patient can cause trauma and irritation to the passage of the patient, and thus it is desirable to minimize the number of times that surgical instruments need to be withdrawn and inserted/reinserted into the patient.

It is conceivable that the surgeon can use the surgical cutting instrument as a suction device, for example, by stopping rotation of the inner cutting tube (if the instrument includes an inner cutting tube) while continuing to apply suction through the inner tube. By careful operation of the pedal (or other control device) which controls the rotation of the inner tube, the surgeon can cause the cutting windows of the inner and outer tubes to be aligned with each other such that suction can be applied to the surgical site through the aligned windows of the inner and outer tubes. However, because the windows of the inner and outer tubes are cutting surfaces (and typically include serrations), most surgeons choose not to use the surgical cutting tool as a suctioning device because tissue adjacent to the outer tube window tends to be drawn into the window and partially cut and/or irritated by the cutting surfaces of the inner and outer tubes. Additionally, because the cutting windows of the inner and outer tubes are disposed on a side surface of the distal tips of the inner and outer tubes, the suction is applied from the side of the distal end of the tube, which is not optimal. Most suction wands apply the suction from the very end of the tip such that suction is applied at the very tip of the suction wand.

According to an aspect of the invention, a surgical instrument can function as a suction wand by providing a suction conduit that is slidably movable over a main unit of the surgical instrument between a retracted position and an extended position. The main unit includes at least one tubular body having a distal end, a proximal end, and an inlet disposed near the distal end. When in the retracted position, the suction conduit does not cover the inlet of the main unit. For example, a distal end of the suction conduit can be located proximal of the inlet of the main unit when in the retracted position so that the main unit of the surgical instrument can be used to perform its operating function (for example, cutting). When the suction conduit is moved to its extended position, the inlet of the main unit is covered and a suction inlet of the suction conduit is in fluid-communication with the main unit inlet. For example, the distal end of the suction conduit and the suction inlet can be located distally beyond the inlet of the main unit when in the extended position. The surgical instrument can be used as a suction tool by placing the suction conduit in the extended position and applying a vacuum through the inlet of the main unit and the suction inlet. The vacuum is directed through the suction inlet near the distal end of the suction conduit so that the suction can be applied from the distal-most tip of the surgical instrument.

In accordance with some embodiments, the distal end of the suction conduit extends beyond the distal end of the main unit when the suction conduit is disposed in the extended position. This helps prevent tissue of the patient from contacting the inlet of the main unit when the surgical instrument is being used to perform a suctioning operation. However, if the inlet of the main unit is positioned far enough away from the distal-most end of the main unit and/or shaped appropriately, it may not be necessary for the distal end of the suction conduit to extend beyond the distal-most end of the main unit in order to avoid having tissue contact the inlet of the main unit during a suctioning operation.

In accordance with some embodiments, the distal end of the suction conduit is open and forms the suction inlet.

The suction conduit also preferably includes an extension/retraction mechanism near a proximal end of the suction conduit. A user of the surgical instrument can use the extension/retraction mechanism to move the suction conduit between the extended and retracted positions. According to some embodiments, the extension/retraction mechanism includes a protruding handle by which the user manually moves the suction conduit between the extended and retracted positions. According to some embodiments, the extension/retraction mechanism includes a spring that biases the suction conduit into at least one of the extended and retracted positions.

According to one embodiment, the extension/retraction mechanism includes a spring and a fixed member having a U-shaped groove with first and second ends. In addition, the extension/retraction mechanism includes a sliding member that moves with the suction conduit between the extended and retracted positions and that has a protrusion that slides within the U-shaped groove. The spring biases the protrusion toward the first and second ends of the groove, and the user moves the suction conduit between the extended and retracted positions by rotating and sliding the sliding member to cause the protrusion to move to one of the first and second ends of the U-shaped groove.

According to preferred embodiments, the main unit and the suction conduit are made from a sterilizable material. The sterilizable material can be a metal such as stainless steel, although other materials also can be used.

In accordance with some aspects of the invention, the surgical instrument can be used in a surgical method that includes inserting the instrument into a passage of a patient and then performing a suctioning operation. The suctioning operation includes disposing the suction conduit in the extended position while applying a vacuum through the main unit to draw material from the passage of the patient into the main unit through the suction inlet of the suction conduit and the inlet of the at least one tubular body of the main unit.

According to some embodiments, the surgical instrument is a cutting instrument and the inlet of the main unit is a cutting window having a cutting edge.

In accordance with one embodiment, the cutting instrument includes an outer cutting blade, an inner cutting blade and the suction conduit. The outer cutting blade has a tubular body with a proximal end and a distal end, with a cutting window disposed at a side of the outer cutting blade near the distal end. The inner cutting blade has a tubular body with a proximal end and a distal end, with a cutting window disposed at a side of the inner cutting blade near the distal end. The inner cutting blade is rotatably disposed inside of the outer cutting blade such that the surgical instrument cuts tissue by rotating the inner cutting blade within the outer cutting blade while a vacuum is applied through an internal bore of the inner cutting blade to draw the tissue into the cutting windows of the outer and inner cutting blades and sever the tissue by rotation of the inner cutting blade. The suction conduit is slidably disposed over the outer cutting blade such that when in its retracted position, the suction conduit does not cover the outer cutting blade cutting window, and when in its extended position, the suction conduit covers the cutting window of the outer cutting blade and a distal end of the suction conduit is located distally beyond the outer cutting blade cutting window. When the surgical instrument is used as a suction tool, the suction conduit is placed in the extended position and the vacuum is applied through the internal bore of the inner cutting blade while the inner cutting blade is stopped from rotating such that the cutting windows of the outer and inner cutting blades communicate with each other. The suction is applied to a passage of the patient through a suction inlet of the suction conduit, which is in fluid-communication with the outer cutting blade cutting window when in the extended position.

In accordance with one aspect of the invention, a surgical method includes inserting the surgical cutting instrument described above into a passage of a patient, and then performing a suctioning operation using the surgical cutting instrument. The suctioning operation includes disposing the suction conduit in its extended position, and positioning the inner cutting blade relative to the outer cutting blade so that the cutting windows of the outer and inner cutting blades communicate with each other while applying a vacuum through the internal bore of the inner cutting blade to draw material from the passage of the patient into the internal bore of the inner cutting blade through the suction inlet of the suction conduit and the cutting windows.

The inner cutting blade can be positioned relative to the outer cutting blade so that the cutting windows communicate with each other by the surgeon operating the controls of the surgical instrument (for example, by operating a foot pedal) while observing the distal tip of the cutting instrument (for example, with an endoscope as is typically used to observe the surgical procedure) until the cutting window of the inner cutting blade is positioned to communicate with the cutting window of the outer cutting blade.

The method of suctioning can be performed after the surgical instrument has been used for cutting (or any other operation that the surgical instrument performs) and/or before the surgical instrument has been used for cutting (or any other operation that it performs). In either case, it is unnecessary to withdraw the surgical instrument when switching between a suctioning operation and its other (for example, cutting) operation. Furthermore, a separate suction wand may not be needed.

BRIEF DESCRIPTION OF THE DRAWINGS

Various exemplary embodiments of the disclosed surgical instrument will be described in detail with reference to the following drawings in which:

FIG. 6 is a side, partial cross-sectional view of an extension/retraction mechanism having a protruding handle that a user can manipulate to move the suction conduit between the extended and retracted positions, FIG. 6 showing the suction conduit in the retracted position;

FIG. 7 is similar to FIG. 6 but shows the suction conduit in the extended position;

DETAILED DESCRIPTION OF EMBODIMENTS

Figure 1:
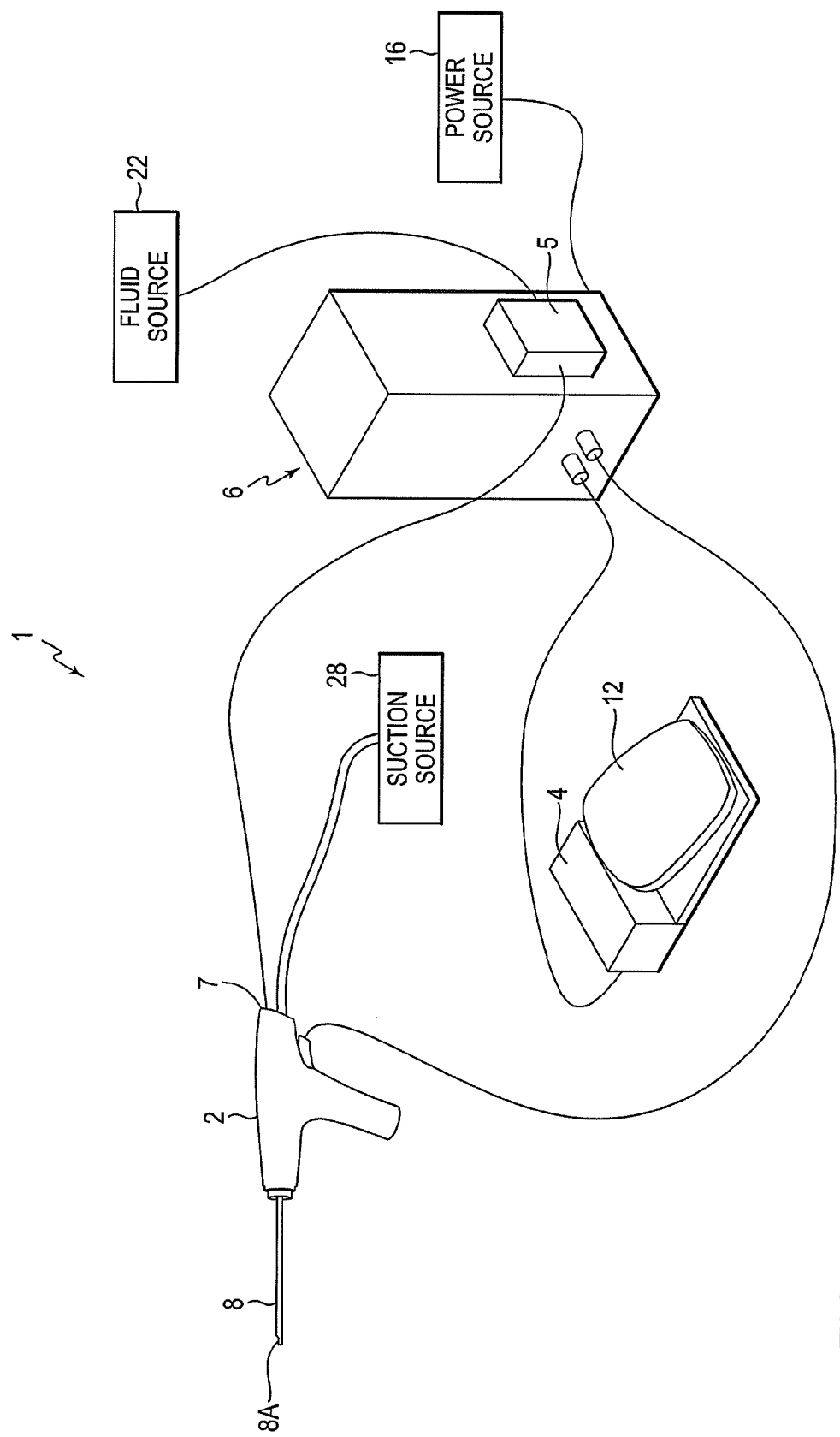
FIG. 1 illustrates a perspective view of a powered surgical tool system that incorporates a surgical instrument, control unit, fluid source and suction source.

The following exemplary embodiments are described below with reference to the figures in the context of human surgery, such as ear, nose and throat surgery, and in particular sinus surgery as well as head and neck surgery. The following exemplary embodiments may also be utilized in spinal surgery, orthopedic surgery, and various other surgical applications. Moreover, the invention is applicable to surgical instruments other than cutting instruments. The invention is applicable to any surgical instrument that is tubular and is provided with suction. All exemplary embodiments of the invention are intended to be used in any applicable field of endeavor.

In the illustrated embodiments, a suction tube is provided to (added to) a surgical cutting instrument. The illustrated surgical cutting instrument includes a main unit having outer and inner cutting blades, each of which is a tubular body having a cutting window located at a side near a distal end of the tubular body. However, the invention is applicable to other surgical cutting instruments, for example, surgical cutting instruments in which the inner cutting blade is not a tubular body having a cutting window. The main unit of the surgical cutting instrument could have, for example, an outer cutting blade having a tubular body with a cutting window at or near its distal end and an inner cutting blade that includes a solid (non-hollow) shaft with a cutting tip at its distal end and that rotates within the outer cutting blade. Suction would be applied through the hollow outer cutting blade.

The surgical instrument also need not be a cutting instrument. For example, the surgical instrument could be a grasping instrument such as forceps or an electrosurgical cauterizing device. The surgical instrument merely should have at least one tubular (hollow) body with an opening near its distal end through which suction can be applied. The suction conduit allows for suction to be applied to the surgical site through a suction inlet of the suction conduit instead of through the inlet of the at least one tubular body so as to either (i) change the location at which the suction will be applied to the surgical site by the surgical instrument (for example, to apply the suction from the distal-most tip of the instrument instead from a side of the distal end of the instrument), or (ii) prevent tissue at the surgical site from contacting the inlet of the at least one tubular body (for example, to prevent the tissue from being irritated by the inlet), or (iii) both change the location at which the suction will be applied to the surgical site and prevent the tissue from contacting the inlet of the at least one tubular body.

In the illustrated embodiments, the suction conduit is a tube having an open distal end that forms the suction inlet of the suction conduit. However, the invention is not limited to the illustrated suction conduit. For example, the suction inlet (or a plurality of suction inlets) could be provided near the distal end of suction conduit (facing either distally or to a side of the suction conduit near the distal end). Although a side-facing suction inlet might not be optimal if the surgeon wants to apply suction at the distal-most end of the surgical instrument, it would still be effective at preventing tissue from contacting the inlet of the at least one tubular body of the surgical instrument in situations where the surgeon wishes to apply suction at a side of the distal end of the surgical instrument.

In the illustrated embodiments, the distal end of the suction conduit extends beyond the distal end of the at least one tubular body (for example, the outer cutting blade) of the surgical instrument main unit when in the extended position. However, depending on the structure of main unit inlet (namely, the location and shape of the inlet), it may not be necessary for the distal end of the suction conduit to extend distally beyond the distal-most end of the main unit when in the extended position. All that is desired is that the suction conduit prevent tissue from contacting the inlet of the main unit when the suction conduit is in the extended position and that the suction inlet of the suction conduit be disposed in a location where the surgeon desires to apply suction to the patient. For example, if the inlet of the main unit is disposed sufficiently proximal of the distal-most tip of the main unit, the distal end of the suction conduit may not need to extend distally beyond the distal-most tip of the main unit when in the extended position.

FIG. 1 is a schematic of a powered surgical tool system. Except for the suction conduit, to be described hereafter, the system may be in accordance with the system described in U.S. Pat. No. 7,247,161, the disclosure of which is incorporated herein by reference in its entirety. Another system to which the invention is applicable is described in U.S. Pat. No. 7,318,831, the disclosure of which is incorporated herein by reference in its entirety. As shown in FIG. 1, the powered surgical tool system 1 includes a handle 2, a footswitch 4 (with pedal 12), fluid (liquid and/or gas) source 22, suction source 28, a control unit 6, fluid pump 5 and a fluid inlet/irrigation outlet 7. The system is supplied with power from a power source 16 such as a wall outlet. The suction source 28 may be an external suction source such as provided by attachment to a facility suction outlet mounted on a wall. The handle 2 is connected, at its distal end, to a surgical instrument 8. The surgical instrument 8 in this embodiment includes a cutting tip at its distal end 8A that is used, for example, to cut, shave, remove, resect and/or abrade tissue, bone and/or other bodily materials.

Figure 2:
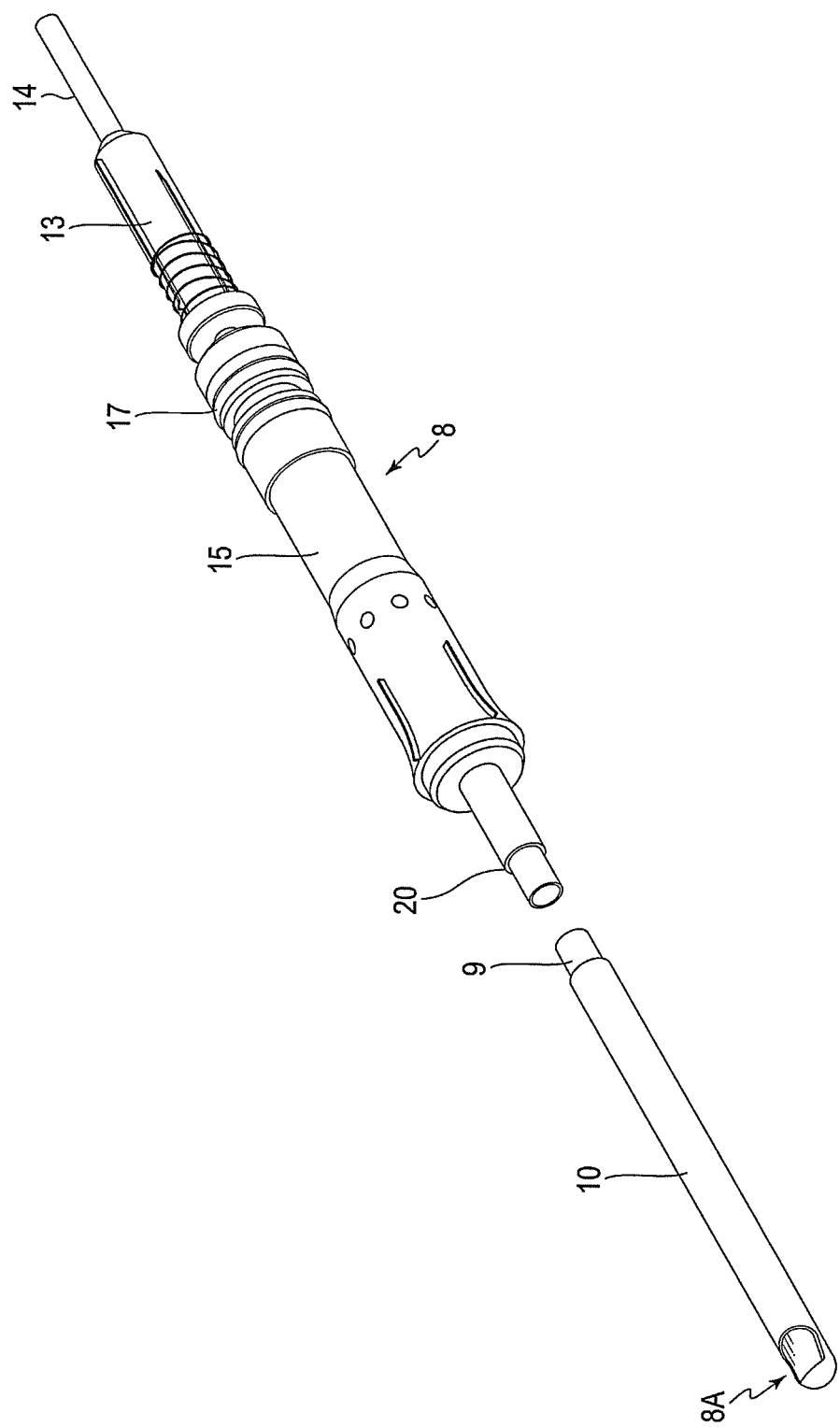
FIG. 2 is a perspective view of an exemplary embodiment of a surgical instrument in accordance with the present disclosure but without the suction conduit being provided.

FIG. 2 illustrates a perspective view of an exemplary embodiment of the surgical instrument 8 without the suction conduit installed. The instrument 8 incorporates an inner tube 9 and an outer tube 10. In this exemplary embodiment, an inner tube hub 13 is formed on the second end 14 of the inner tube 9 and an outer tube hub 15 is formed on the second end 17 of the outer tube 10. The inner tube 9 is inserted into a fluid passage 20 formed within the outer tube 10 so that the inner tube 9 is co-axially disposed within the outer tube 10 until the external distal tip of the inner tube 9 contacts the internal distal surface of the outer tube 10. The outer tube 10 has a larger diameter than the inner tube 9, thus allowing for insertion of the inner tube 9 within the outer tube 10. However, it should be appreciated that the inner and outer tubes will be pre-assembled prior to delivery to the customer. Thus, a customer will most likely not be inserting the inner tube into the outer tube.

The inner and outer tube hubs 13, 15 couple the inner and outer tubes 9, 10, respectively, to the handle 2. Once coupled to the handle 2, the outer tube 10 will be fixed relative to the handle 2, but the inner tube 9 will be rotatable relative to the outer tube 10 and the handle 2.

Figure 3:
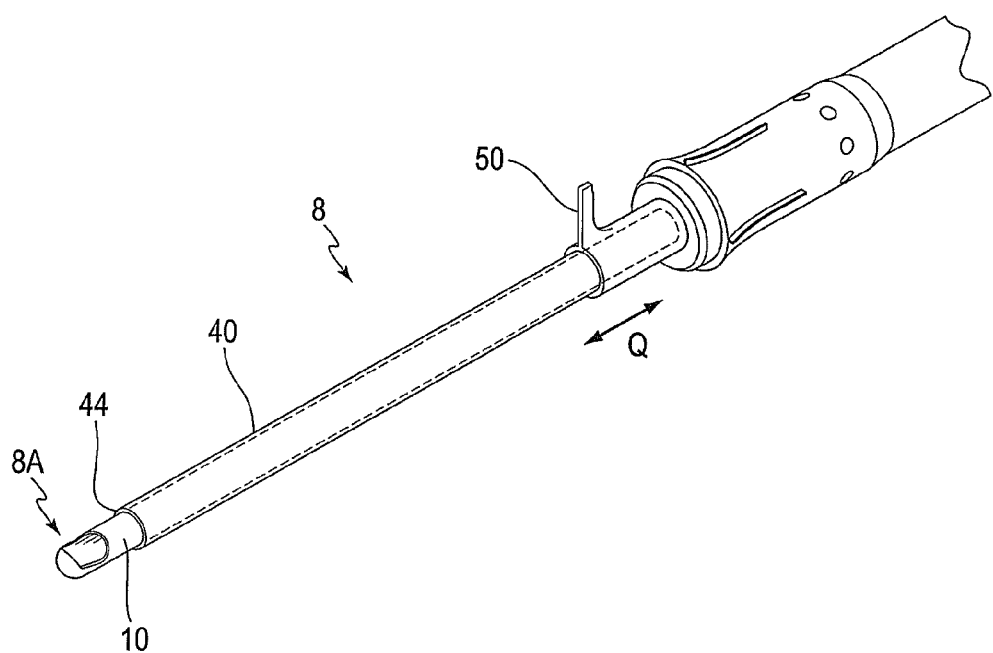
FIG. 3 is a perspective view similar to FIG. 2 except that a suction conduit according to an exemplary embodiment is provided.

FIG. 3 is a perspective view of the surgical instrument 8 with the suction conduit 40 installed over (attached to) the outer tube 10. The suction conduit 40 is movably slidable as shown by the arrows Q in FIG. 3 between a retracted position shown in FIGS. 3 and 4 at which the tip 8A is uncovered, and an extended position shown in FIG. 5 in which a suction inlet 44 located at a distal end of the suction conduit 40 extends beyond the distal tip of the outer tube 10.

Before describing operation of the suction conduit 40 in detail, an embodiment relating to a surgical cutting instrument will be described. The surgical cutting instrument includes the structure shown in FIG. 2 in which an inner tube 9 is disposed within an outer tube 10. The outer tube 10 includes a cutting window 60 (see FIGS. 4 and 5) disposed at a side of its distal end. Thus, the outer tube 10 can be referred to as an outer cutting blade. The inner tube 9 also includes a cutting window 30 (see FIGS. 4 and 5) disposed at a side of its distal end. Thus, the inner tube 9 can be referred to as an inner cutting blade. The edges of the cutting windows 30 and 60 can be serrated, smooth or a combination of serrated and smooth to form cutting surfaces. As mentioned previously, the inner cutting blade 9 rotates within the outer cutting blade 10, and thus as the inner cutting blade 9 rotates, the cutting windows 30 and 60 become aligned with each other (they communicate with each other) as shown in FIG. 4 and then become misaligned with each other during rotation (not shown).

The outer cutting blade 10 thus is a tubular body having a proximal end and a distal end, with the cutting window 60 disposed at a side of the outer cutting blade 10 near the distal end.

The inner cutting blade 9 is a tubular body having a proximal end and a distal end, with the cutting window 30 disposed at a side of its distal end. As mentioned previously, the inner cutting blade 9 is rotatably disposed inside of the outer cutting blade 10 such that the surgical instrument 8 cuts tissue by rotating the inner cutting blade 9 within the outer cutting blade 10 while a vacuum is applied through an internal bore 25 of the inner cutting blade 9 to draw the tissue into the cutting windows 30 and 60 of the cutting blades 9 and 10 and sever the tissue by rotation of the cutting blade 9.

Figure 4:
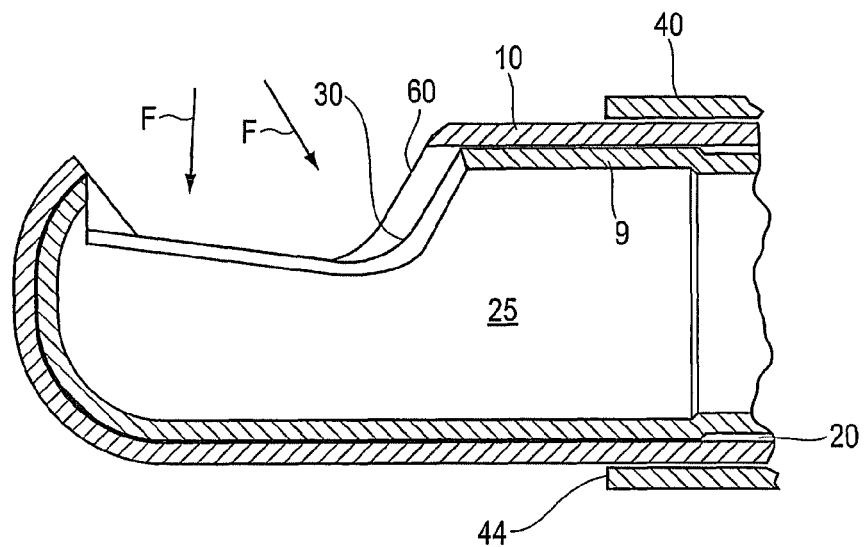
FIG. 4 is a side, cross-sectional view of the distal tip of the surgical instrument showing the suction conduit in the retracted position.

The surgical instrument 8 can be used as a suction tool by applying the vacuum through the internal bore 25 of the cutting blade 9 while the cutting blade 9 is stopped from rotating and the cutting windows 30 and 60 of the cutting blades 9 and 10 communicate with each other as shown in FIG. 4 (and FIG. 5) so that the vacuum is applied through the opening defined by the communicating (or aligned) cutting windows 30 and 60. The surgeon operating the instrument 8 can cause the windows 30 and 60 to become oriented in a state in which the windows communicate with each other by, for example, tapping on the pedal 12 that controls the instrument to cause incremental rotation of the inner cutting blade 9 while observing the distal tip of the instrument, for example, by an endoscope, which usually also is disposed at the operating site, until the windows 30 and 60 obtain the state shown in FIGS. 4 and 5. With the windows 30 and 60 communicating with each other as shown in FIGS. 4 and 5, vacuum can be applied through the internal bore 25 of the cutting blade 9 so that the surgical instrument can be used like a suction wand.

However, if the surgical instrument is used like a suction wand when in the state shown in FIG. 4 (with the suction conduit 40 in its retracted position) tissue tends to come into contact with one or both of the cutting blades 30 and 60, which can either cut the tissue or irritate the tissue. Furthermore, the suction is applied from the side of the distal tip, which is not preferred by surgeons in many situations. The flow that occurs when the suction conduit 40 is retracted, for example, during performance of a cutting operation, is illustrated by arrows F in FIG. 4.

Figure 5:
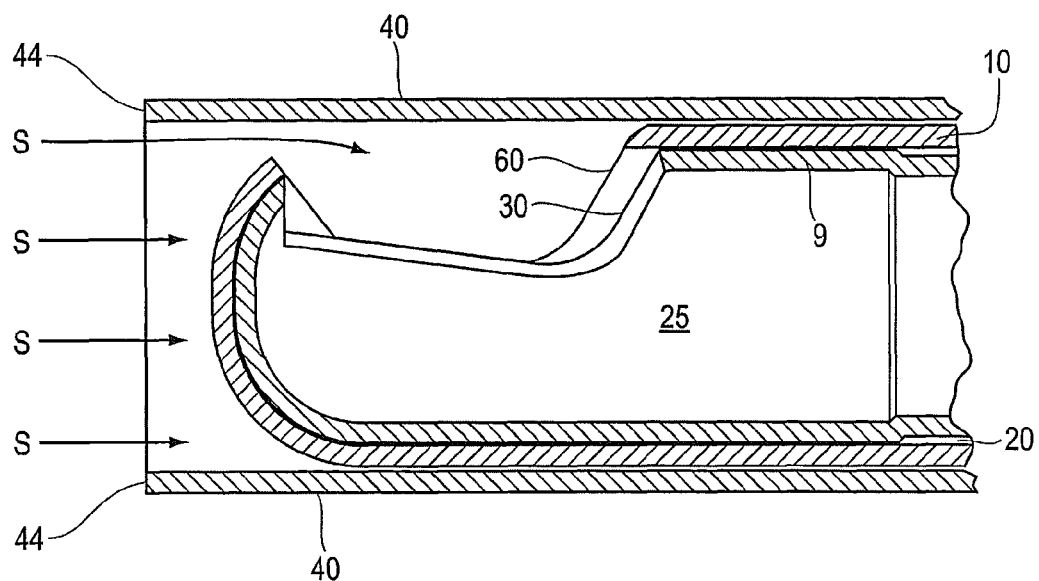
FIG. 5 is a side, cross-sectional view similar to FIG. 4 but with the suction conduit in the extended position to perform a suctioning operation.

Accordingly, when it is desired to perform a suctioning operation, the suction conduit 40 is moved to its extended position as shown in FIG. 5. When in the extended position, the distal end of the suction conduit 40 extends beyond the opening defined by the cutting windows 30 and 60 so as to cover that opening and thereby prevent tissue from entering the opening and possibly becoming irritated by the cutting edges of the cutting windows 30 and/or 60. In some embodiments, and as illustrated in FIG. 5, the distal tip of the suction conduit 40 extends beyond the distal-most end of the outer cutting blade 10 such that the suction inlet 44 of the suction conduit 40 also extends distally beyond the distal-most end of the outer cutting blade 10. The flow of fluid into the suction inlet 44 of the suction conduit 40 is shown by the arrows S in FIG. 5. As can be appreciated, tissue will not come into contact with the opening defined by the cutting windows 30 and 60. Furthermore, the suction is applied from the distal-most tip of the surgical instrument, which usually is preferred by surgeons. As also will be appreciated from FIG. 5, a first gap exists between an inner surface of the suction conduit 40 and a distal-most edge of the aligned cutting windows 30 and 60, and a second gap, smaller than the first gap, exists between the inner surface of the suction conduit 40 and an outermost surface of the tubular body of the outer cutting blade 10 on a side of the outer cutting blade 10 opposite from the aligned cutting windows 30 and 60, so that fluid will flow through the suction inlet 44, the first gap and the aligned cutting windows 30/60 when a vacuum is applied through an internal bore 25 of the inner cutting blade 9.

Although it is not necessary, irrigation fluid also could be supplied through bore 20 when in the state shown in FIG. 5.

The cutting blades 9 and 10, as well as the suction conduit 40, are made from a sterilizable material. According to some embodiments, the sterilizable material is a metal such as stainless steel.

Furthermore, it is preferable to make the suction conduit 40 from a stiff material (such as stainless steel) because that will enable the suction conduit 40 to be made as thin as possible. It is desirable to make the suction conduit 40 as thin as possible so that the overall diameter of the surgical instrument is not increased significantly due to the presence of the suction conduit 40.

When the instrument is used for surgery, the surgical instrument is inserted into a passage of a patient. Either before or after (or both before and after) a cutting operation is performed, the surgical instrument can be used to perform a suctioning operation. The suctioning operation includes moving the suction conduit 40 to its extended position, and positioning the inner cutting blade 9 relative to the outer cutting blade 10 so that the cutting windows 30 and 60 communicate with each other while vacuum is applied through the internal bore 25 of the inner cutting blade 9 to draw material from the passage of the patient into the internal bore 25 through the suction inlet 44 of the suction conduit 40 and through the cutting windows 30 and 60. During performance of the suctioning operation, the inner cutting blade 9 is not rotated relative to the outer cutting blade 10.

Thus, it is unnecessary to withdraw the surgical cutting instrument 8 from the patient when switching between a cutting operation and a suctioning operation. Moreover, a separate suctioning wand may not be needed. Thus, the surgical procedure that is performed with the surgical instrument 8 can be performed more quickly and while causing less trauma to the patient.

In the illustrated embodiments, the inner and outer cutting blades 9 and 10 and the suction conduit 40 are straight and rigid. However, the surgical instrument 8 can have one or more bends in it such that it is not straight. In such an arrangement, at least the inner cutting blade 9 and the suction conduit 40 would be flexible. Flexible hollow tubes (including hollow cutting blades) are known and used with curved cutting instruments. See, for example, U.S. Pat. No. 4,646,738, the disclosure of which is incorporated herein by reference in its entirety, and see, for example, U.S. Pat. No. 5,707,350, the disclosure of which is incorporated herein by reference in its entirety.

It also is preferable to provide additional structure to enable the suction conduit 40 to be easily moved between the extended and retracted positions. Thus, an extension/retraction mechanism is provided for the suction conduit 40 by which the suction conduit 40 is moved between the retracted and extended positions. The extension/retraction mechanism can be a simple gripping member attached to the suction conduit 40 that the user (surgeon) grasps to slide the suction conduit 40 along the main unit, or it could include a device to assist in the sliding movement, for example, one or more springs to bias the suction conduit 40 toward one or both of the retracted and extended positions. Preferably, the extension/retraction mechanism is located near a proximal end of the suction conduit 40 so that the user can readily manipulate the extension/retraction mechanism while still holding the handle of the surgical instrument. FIG. 3 shows a protruding handle 50 that is an extension/retraction mechanism that a user of the instrument can grasp so as to move the suction conduit 40 between its extended and retracted positions.

FIGS. 6 and 7 provide more detail on the extension/retraction mechanism having the protruding handle 50. FIG. 6 shows the suction conduit 40 and extension/retraction mechanism when the suction conduit 40 is in the retracted position, whereas FIG. 7 shows the positions of the suction conduit 40 and the protruding handle 50 when in the extended position. The handle 50 is fixed to the suction conduit 40. The proximal end of the protruding handle 50 abuts a surface 19 of the handpiece 2 to position the suction conduit 40 in the retracted position as shown in FIG. 6. A rib 52 or other protruding member is provided on an external surface of the outer cutting blade 10. An engaging recess 56 is provided in the internal surface of the handle 50. As shown in FIG. 7, the rib 52 engages with the recess 56 to hold the handle 50 and the attached suction conduit 40 in the extended position when the user moves the handle 50 away from the handpiece 2 into the extended position.

Although the embodiment shown in FIGS. 6 and 7 is simple, it can be difficult for the surgeon to readily move the protruding handle 50 and the attached suction conduit 40 between the extended and retracted positions while holding the handle 2. Thus, it can be desirable to provide the extension/retraction mechanism with a member, for example, a spring, which provides a motive force to assist in moving the suction conduit 40 between the extended and retracted positions. The second embodiment of extension/retraction mechanism described below provides such a member.

Figure 8:
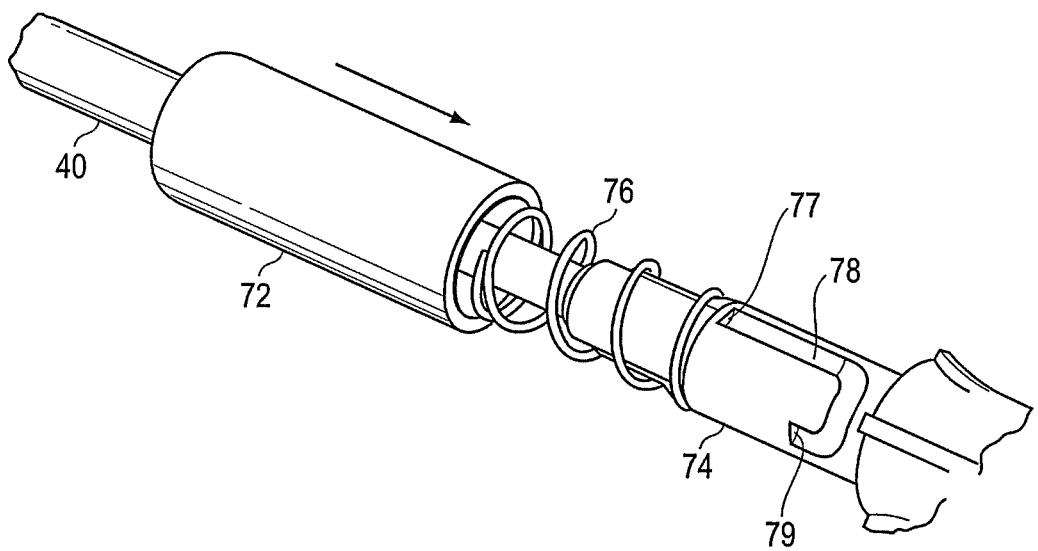
FIG. 8 is an exploded view of a spring biased extension/retraction mechanism.
Figure 9:
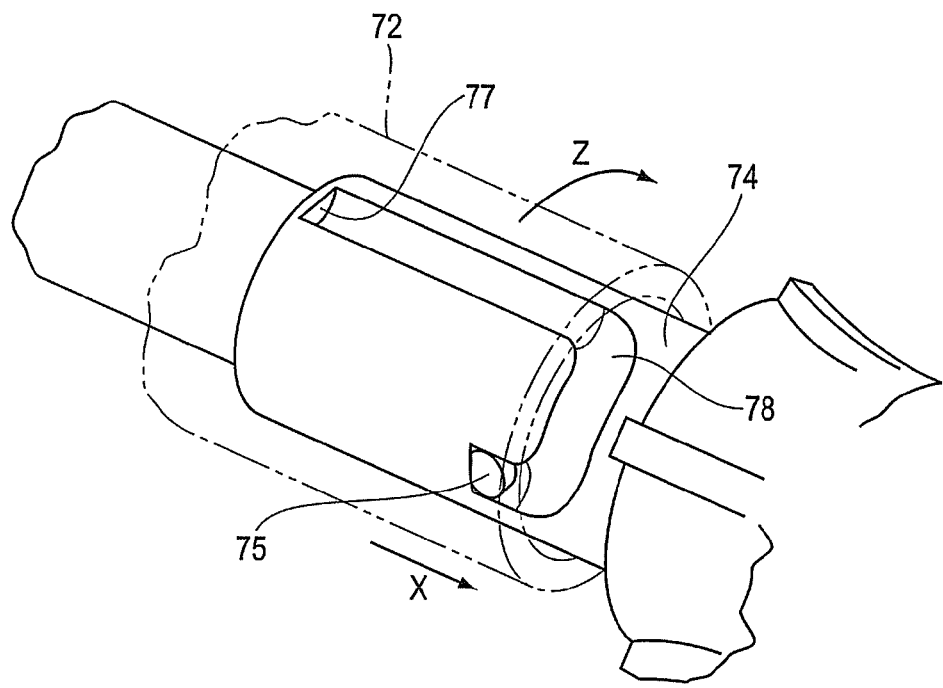
FIG. 9 shows the FIG. 8 embodiment in the retracted position.
Figure 10:
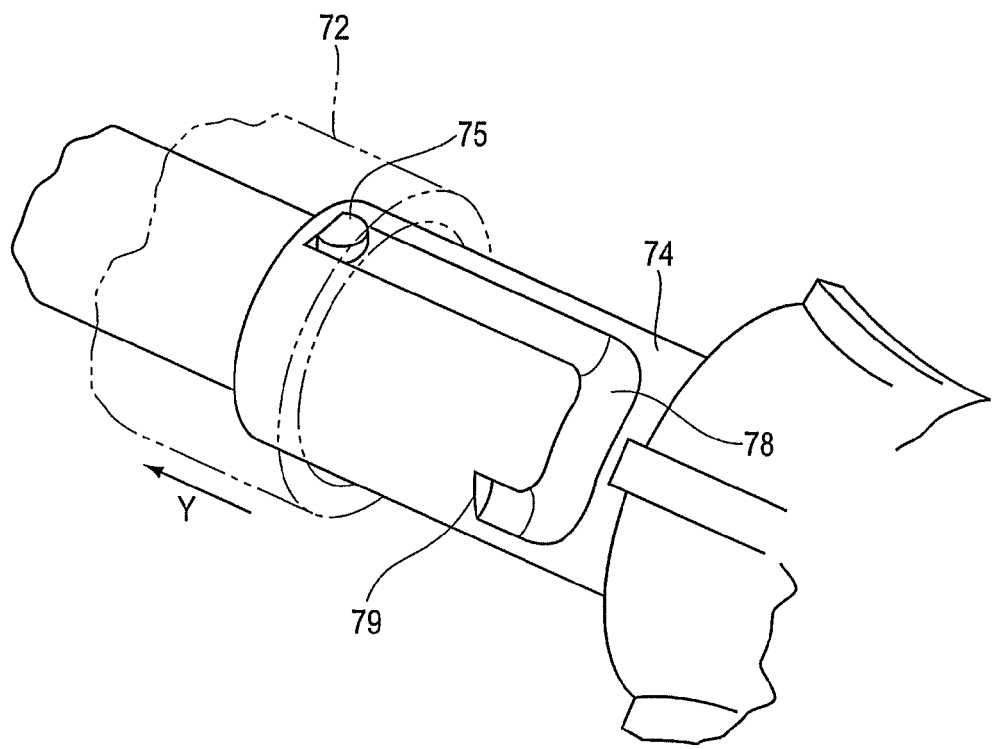
FIG. 10 shows the FIG. 8 embodiment in the extended position.

FIGS. 8-10 illustrate an embodiment in which a spring 76 is used to bias the suction conduit 40 into both the extended and retracted positions. The extension/retraction mechanism of FIGS. 8-10 includes a sliding member 72 that is attached (fixed) to the suction conduit 40, a fixed member 74 that does not move and that is fixed to the handpiece 2 and/or to the outer blade 10 at its proximal end, and spring 76 which extends between the sliding member 72 and the fixed member 74. The internal surface of the sliding member 72 is cylindrical and includes a protrusion 75 that protrudes radially inward towards the central, longitudinal axis of the sliding member 72. The protrusion 75 slides within a U-shaped groove 78 formed in an external surface of the fixed member 74. The U-shaped groove 78 includes a first end 77 and a second end 79.

The user of the surgical instrument slides and rotates the sliding member 72 in order to move the sliding member 72 and the suction conduit 40 fixed thereto between the extended and retracted positions. FIG. 9 shows the retracted position. While in the retracted position, the protrusion 75 engages the second end 79 of the U-shaped groove 78. In order to move the suction conduit 40 from the retracted position to the extended position, the user first moves the sliding member 72 proximally as shown by arrow X in FIG. 9, and then rotates the sliding member 72 as shown by the arrow Z in FIG. 9. Then, the user permits the sliding member 72 to move in the direction of arrow Y in FIG. 10, assisted by the biasing force supplied by the spring 76 until the protrusion 75 engages the first end 77 of the U-shaped groove as shown in FIG. 10. The user slides and rotates the sliding member 72 in the opposite sequence to return the suction conduit 40 to its retracted position. The extension/retraction mechanism of FIGS. 8-10 is easier for the surgeon to manipulate while still holding the handle 2. Furthermore, it is easier to properly place the suction conduit in its extended position compared to the embodiment of FIGS. 6-7.

Other mechanisms having one or more spring or other biasing member(s) could be used for moving the suction conduit. For example, a spring-biased mechanism similar to what is used in many ballpoint pens can be used as the extension/retraction mechanism in order to move the suction conduit 40 between its extended and retracted positions. One potential benefit of such an embodiment is that the user only needs to press a button in order to cause the suction conduit 40 to move between the extended and retracted positions.

The illustrated exemplary embodiments of the surgical tool as set forth above are intended to be illustrative and not limiting. Various changes may be made without departing from the spirit and scope of the invention.

What is claimed is:

1. A surgical instrument comprising:
a tubular body with a proximal end and a distal end, a window disposed at a side of the tubular body near the distal end; and
a suction conduit attached to and slidably disposed over the tubular body before the surgical instrument is inserted into a patient, the suction conduit being slidably movable along the tubular body between a retracted position, at which the suction conduit does not cover the window of the tubular body, and an extended position at which the suction conduit covers the window of the tubular body and a distal end of the suction conduit is located distally beyond the window of the tubular body, the suction conduit including a suction inlet at the distal end of the suction conduit, the distal end of the suction conduit is open to form the suction inlet, and the distal end of the suction conduit is located proximal of the window of the tubular body when the suction conduit is in the retracted position,
wherein the tubular body is configured such that when the suction conduit is in the extended position, a first gap exists between an inner surface of the suction conduit and a distal-most edge of the window and a second gap, smaller than the first gap, exists between the inner surface of the suction conduit and an outermost surface of the tubular body on a side of the tubular body opposite from the window, such that fluid flows through the suction inlet, the first gap and the window when a vacuum is applied through an internal bore of the tubular body.

2. The surgical instrument of claim 1, wherein the distal end and the suction inlet of the suction conduit extend beyond the distal end of the tubular body when the suction conduit is in the extended position.

3. The surgical instrument of claim 1, wherein the suction conduit is metallic.

4. The surgical instrument of claim 1, wherein the suction conduit is rigid.

5. The surgical instrument of claim 1, wherein the suction conduit includes an extension/retraction mechanism near a proximal end of the suction conduit by which a user of the surgical instrument moves the suction conduit between the extended and retracted positions.

6. The surgical instrument of claim 5, wherein the extension/retraction mechanism includes a protruding handle by which the user manually moves the suction conduit between the extended and retracted positions.

7. The surgical instrument of claim 5, wherein the extension/retraction mechanism includes a spring that biases the suction conduit into at least one of the extended and retracted positions.

8. The surgical instrument of claim 7, wherein the extension/retraction mechanism further includes a fixed member having a U-shaped groove with first and second ends, and a sliding member that moves with the suction conduit between the extended and retracted positions and that has a protrusion that slides within the U-shaped groove, wherein the spring biases the protrusion toward the first and second ends, and the user moves the suction conduit between the extended and retracted positions by rotating and sliding the sliding member to cause the protrusion to move to one of the first and second ends of the U-shaped groove.

9. The surgical instrument of claim 1, wherein the tubular body and the suction conduit are made from a sterilizable material.

10. The surgical instrument of claim 9, wherein the sterilizable material is metal.

11. The surgical instrument of claim 1, wherein the tubular body and the suction conduit are made from stainless steel.

12. A surgical method comprising:
 inserting the surgical instrument of claim 1 into a passage of a patient; and
 performing a suctioning operation, the suctioning operation including:
  disposing the suction conduit in the extended position, and
  applying the vacuum through the internal bore of the tubular body to draw material from the passage of the patient into the internal bore of the tubular body through the suction inlet of the suction conduit and the window of the tubular body.

13. A surgical instrument comprising:
 a tubular body with a proximal end and a distal end, a window disposed at a side of the tubular body near the distal end;
 a suction conduit attached to and slidably disposed over the tubular body before the surgical instrument is inserted into a patient, the suction conduit being slidably movable along the tubular body between a retracted position, at which the suction conduit does not cover the window of the tubular body, and an extended position at which the suction conduit covers the window of the tubular body and a distal end of the suction conduit is located distally beyond the window of the tubular body, the suction conduit including a suction inlet at the distal end of the suction conduit; and
 an inner tubular conduit with a proximal end and a distal end, a window disposed at a side of the inner tubular conduit near the distal end, the inner tubular conduit movably disposed inside of the tubular body, wherein
 the tubular body is configured such that when the suction conduit is in the extended position, a first gap exists between an inner surface of the suction conduit and a distal-most edge of the window and a second gap, smaller than the first gap, exists between the inner surface of the suction conduit and an outermost surface of the tubular body on a side of the tubular body opposite from the window, such that fluid flows through the suction inlet, the first gap and the window when a vacuum is applied through an internal bore of the tubular body, and
 the inner tubular conduit and the tubular body are configured such that when the inner tubular conduit and the tubular body are oriented with their windows in alignment and the suction conduit is in the extended position, the fluid flows through the suction inlet, the first gap and the aligned windows when the vacuum is applied through an internal bore of the inner tubular conduit.

14. The surgical instrument of claim 13, wherein the inner tubular conduit is rotatable within the tubular body.

15. The surgical instrument of claim 13, wherein the surgical instrument can be used as a suction tool by placing the suction conduit in the extended position and applying the vacuum through the internal bore of the inner tubular conduit while the inner tubular conduit is stopped from moving relative to the tubular body with the windows of the tubular body and the inner tubular conduit positioned relative to each other so that the vacuum is applied through the windows and the suction inlet of the suction conduit.

16. The surgical instrument of claim 13, wherein a passage exists between the tubular body and the inner tubular conduit through which a liquid can be supplied.

17. A surgical method comprising:
 inserting the surgical instrument of claim 13 into a passage of a patient; and
 performing a suctioning operation, the suctioning operation including:
  disposing the suction conduit in the extended position,
  positioning the inner tubular conduit relative to the tubular body so that the windows communicate with each other, and
  applying the vacuum through the internal bore of the inner tubular conduit to draw material from the passage of the patient into the internal bore of the inner tubular conduit through the suction inlet of the suction conduit and the windows.

18. The surgical method of claim 17, wherein the inner tubular conduit is not moved relative to the tubular body during the step of applying the vacuum.

* * * * *